United States Patent
Ha et al.

(10) Patent No.: US 10,507,135 B2
(45) Date of Patent: Dec. 17, 2019

(54) OPHTHALMIC TREATMENT APPARATUS AND TREATMENT BEAM RADIATING METHOD FOR SAID APPARATUS

(71) Applicant: LUTRONIC VISION INC, Burlington, MA (US)

(72) Inventors: Tae Ho Ha, Goyang (KR); Sang Hoon Lee, Seoul (KR)

(73) Assignee: LUTRONIC VISION INC., Burlington, MA (US)

( * ) Notice: Subject to any disclaimer, the term of this patent is extended or adjusted under 35 U.S.C. 154(b) by 483 days.

(21) Appl. No.: 14/414,691

(22) PCT Filed: Jul. 15, 2013

(86) PCT No.: PCT/KR2013/006324
§ 371 (c)(1),
(2) Date: Jan. 13, 2015

(87) PCT Pub. No.: WO2014/011012
PCT Pub. Date: Jan. 16, 2014

(65) Prior Publication Data
US 2015/0202457 A1   Jul. 23, 2015

(30) Foreign Application Priority Data
Jul. 13, 2012   (KR) ........................ 10-2012-0076776

(51) Int. Cl.
*A61F 9/008* (2006.01)
*A61N 5/06* (2006.01)
*A61N 5/067* (2006.01)

(52) U.S. Cl.
CPC ............ *A61F 9/008* (2013.01); *A61N 5/0613* (2013.01); *A61F 2009/00863* (2013.01);
(Continued)

(58) Field of Classification Search
CPC .............. A61B 3/14; A61B 3/145; A61B 3/15
See application file for complete search history.

(56) References Cited

U.S. PATENT DOCUMENTS

| 4,838,682 A * | 6/1989 | Portnoy | A61B 3/107 |
| | | | 351/211 |
| 2004/0059321 A1* | 3/2004 | Knopp | A61B 3/13 |
| | | | 606/10 |

(Continued)

FOREIGN PATENT DOCUMENTS

| KR | 10-2009-0080976 A | 7/2009 |
| KR | 10-2010-0015565 A | 2/2010 |

OTHER PUBLICATIONS

International Search Report for PCT/KR2013/006324 filed on Jul. 15, 2013.

*Primary Examiner* — Christopher A Flory
*Assistant Examiner* — Nathan A Baldwin

(57) ABSTRACT

The present invention relates to an ophthalmic treatment apparatus and to a treatment beam radiating method for the apparatus. The ophthalmic treatment apparatus according to the present invention comprises: a beam generating unit for generating a treatment beam; a beam delivery unit for delivering the treatment beam generated by the beam generating unit to the retinal region of an eyeball; an image unit for forming an image of the retinal region of the eyeball in the horizontal direction with respect to the plane of the focal spot of the treatment beam guided by the beam delivery unit; and a control unit for controlling the beam delivery unit such that the location of the plane of the focal spot can be adjusted based on the curvature of the retinal region of the eyeball imaged by the image unit.

6 Claims, 5 Drawing Sheets

(52) U.S. Cl.
CPC ............... *A61F 2009/00882* (2013.01); *A61N 2005/067* (2013.01); *A61N 2005/0626* (2013.01); *A61N 2005/0644* (2013.01)

(56) References Cited

U.S. PATENT DOCUMENTS

| | | | |
|---|---|---|---|
| 2009/0268154 A1 | 10/2009 | Meyers et al. | |
| 2010/0290007 A1* | 11/2010 | Van de Velde | A61B 3/102 351/221 |
| 2011/0196350 A1* | 8/2011 | Friedman | A61F 9/008 606/6 |
| 2011/0211162 A1 | 9/2011 | Thibos et al. | |

* cited by examiner

OPHTHALMIC TREATMENT APPARATUS AND TREATMENT BEAM RADIATING METHOD FOR SAID APPARATUS

BACKGROUND OF THE INVENTION

Field of the Invention

The present invention relates to an ophthalmic treatment apparatus and a method for radiating a beam for treatment using the same and, more particularly, to an ophthalmic treatment apparatus for treating a lesion of an eyeball by radiating a beam for treatment, such as a laser, to the lesion of the eyeball and a method for radiating a beam for treatment using the same.

Related Art

Recently, a medical treatment apparatus using a beam, such as a laser, is widely used in various medical fields, such as surgery, dermatology, and ophthalmology. In particular, an ophthalmic treatment apparatus of medical treatment apparatuses uses a laser as a beam for treatment and treats a lesion by radiating a laser to a lesion region, such as the retina of an eyeball.

Meanwhile, a conventional treatment apparatus is disclosed in "U.S. Pat. No. 5,549,596" entitled SELECTIVE LASER TARGETING OF PIGMENTED OCULAR CELLS." The aforementioned prior art document discloses a technology capable of reducing the time taken for treatment by radiating a plurality of lasers to a lesion of a patient in a pattern of a specific region.

However, although the treatment apparatus disclosed in the conventional prior art document radiates a plurality of spots like a pattern using a laser in order to reduce the time taken for treatment, there is a problem in that an error may occur in a lesion region having curvature, such as the retina, because the plurality of spots is radiated to the same plane as of focal spots.

SUMMARY OF THE INVENTION

An object of the present invention is to provide an ophthalmic treatment apparatus having an improved method for radiating a beam for treatment so that a beam for treatment is radiated to a treatment region of an eyeball having curvature along the curvature and a method for radiating a beam for treatment using the same.

In accordance with the present invention, means for solving the object is achieved by an ophthalmic treatment apparatus, including a beam generation unit which generates a beam for treatment, a beam delivery unit which guides the beam for treatment generated by the beam generation unit to the retina region of an eyeball, an image unit which generates an image of the retina region of the eyeball in a direction perpendicular to the plane of a focal spot of the beam for treatment that is guided by the beam delivery unit, and a control unit which controls the beam delivery unit so that a location of the plane of the focal spot to which the beam for treatment is radiated is controlled based on curvature of the retina region of the eyeball photographed by the image unit.

In this case, the plane of the focal spot may include the plane of a first focal spot that forms a tangential plane in the arc of the retina region of the eyeball through which the optical axial line of the beam for treatment penetrates and the plane of a second focal spot which is parallel to the plane of the first focal spot along the optical axial line and connects both sides of an arc formed with the contact point of the retina region interposed between the two sides.

A separation distance D between the plane of the first focal spot and the plane of the second focal spot preferably may correspond to the curvature of the retina region of the eyeball.

Furthermore, the beam delivery unit preferably guides the beam for treatment to the retina region of the eyeball in the form of a pattern including a plurality of focal spots.

In this case, the form of the pattern may include a reference pattern radiated to the plane of the first focal spot along the curvature of the retina region of the eyeball and a control pattern radiated to the plane of the second focal spot along the curvature of the retina region of the eyeball.

The beam delivery unit may include a first scanner which guides the beam for treatment generated by the beam generation unit to the plane of the focal spot, a collimation unit which collimates the beam for treatment incident from the first scanner to the retina region of the eyeball, and a second scanner which is disposed between the first scanner and the collimation unit and controls the location of the focal spot of the beam for treatment incident from the first scanner along the optical axial line of the beam for treatment.

Furthermore, the second scanner may include a beam extension lens which extends the beam for treatment incident from the first scanner and a mobile lens which relatively moves compared to the beam extension lens so that the beam for treatment passing through the beam extension lens is radiated along the optical axial line between the plane of the first focal spot and the plane of the second focal spot.

Furthermore, the ophthalmic treatment apparatus may further include an image analysis unit which analyzes the image of the retina region of the eyeball transmitted by the image unit and measures the separation distance between the plane of the first focal spot and the plane of the second focal spot.

In this case, the control unit preferably may control the operation of the beam delivery unit so that the beam for treatment is radiated to the plane of the first focal spot and the plane of the second focal spot based on the separation distance between the plane of the first focal spot and the plane of the second focal spot which has been measured by the image analysis unit.

In contrast, the ophthalmic treatment apparatus may further include an image analysis unit which analyzes the image of the retina region of the eyeball transmitted by the image unit and measures the separation distance between the plane of the first focal spot and the plane of the second focal spot.

In this case, the control unit preferably may relatively move the mobile lens compared to the beam extension lens so that the pattern form of the beam for treatment is radiated to the plane of the first focal spot and the plane of the second focal spot based on the separation distance between the plane of the first focal spot and the plane of the second focal spot which has been measured by the image analysis unit.

Meanwhile, in accordance with the present invention, means for solving the object is also achieved by a method for radiating, by an ophthalmic treatment apparatus, a beam for treatment, including steps of (a) generating an image of the retina region of an eyeball in a direction perpendicular to the plane of a focal spot to which a beam for treatment is radiated, (b) analyzing curvature of the image and measuring a location where the beam for treatment is radiated, and (c) radiating the beam for treatment along the curvature in accordance with the curvature of the image.

In this case, the plane of the focal spot may include the plane of a first focal spot that forms a tangential plane in the arc of the retina region of the eyeball through which the optical axial line of the beam for treatment penetrates and the plane of a second focal spot which is parallel to the plane of the first focal spot along the optical axial line and connects both sides of an arc with the contact point of the retina region interposed between the two sides.

Furthermore, the step (b) may include a step of measuring a separation distance between the plane of the first focal spot and the plane of the second focal spot.

The step (c) may include a step of radiating in the form of a pattern, including a plurality of focal spots, to the plane of the first focal spot and the plane of the second focal spot along the curvature of the image.

In this case, the pattern form may include a reference pattern radiated to the plane of the first focal spot and a control pattern radiated to the plane of the second focal spot with the reference pattern interposed between the control pattern and the plane of the second focal spot.

The details of other embodiments are included in the detailed description and the drawings.

The ophthalmic treatment apparatus and the method for radiating a beam for treatment using the same according to the present invention have the following advantages.

Curvature according to an image of an eyeball is measured and analyze, and the plane of a focal spot to which a beam for treatment is radiated is controlled along the curvature of the eyeball. Accordingly, a beam for treatment can be radiated to a location corresponding to the curvature of an eyeball, thereby being capable of improving treatment efficiency of the eyeball.

DESCRIPTION OF EXEMPLARY EMBODIMENTS

Hereinafter, an ophthalmic treatment apparatus and a method for radiating a beam for treatment using the same in accordance with embodiments of the present invention are described in detail with reference to the accompanying drawings.

Figure 1:
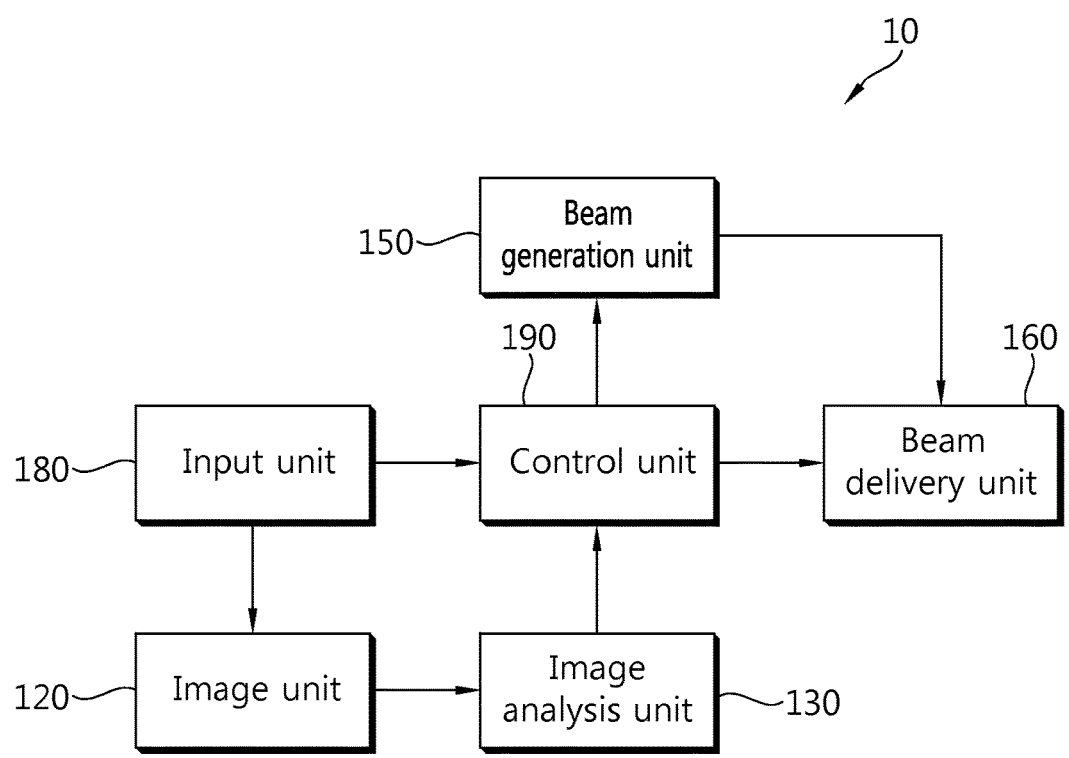
FIG. 1 is a control block diagram of an ophthalmic treatment apparatus in accordance with an embodiment of the present invention.
Figure 2:
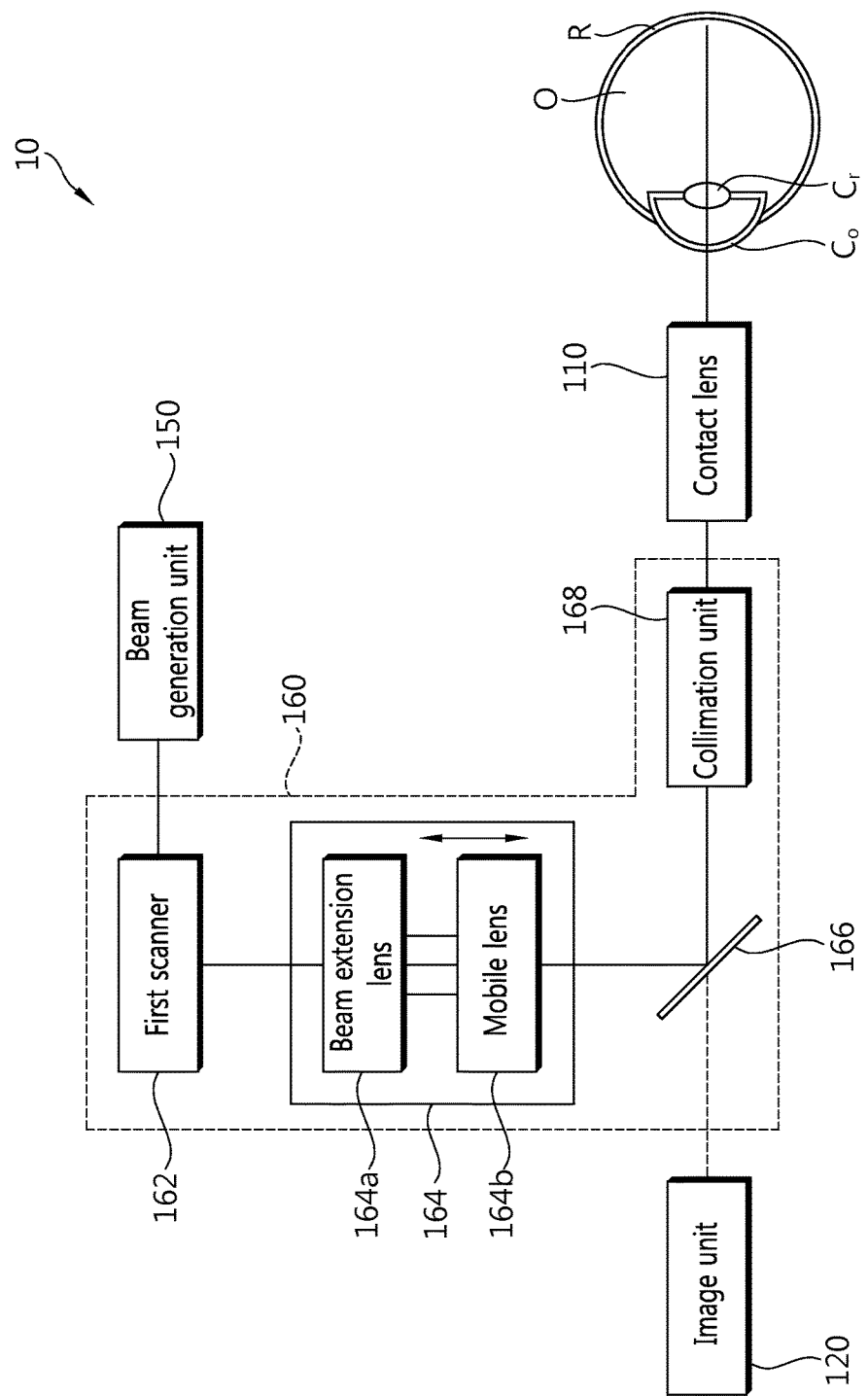
FIG. 2 is a schematic configuration diagram of the ophthalmic treatment apparatus in accordance with an embodiment of the present invention.

FIG. 1 is a control block diagram of an ophthalmic treatment apparatus in accordance with an embodiment of the present invention, and FIG. 2 is a schematic configuration diagram of the ophthalmic treatment apparatus in accordance with an embodiment of the present invention.

As illustrated in FIG. 1 and FIG. 2, the ophthalmic treatment apparatus 10 in accordance with an embodiment of the present invention includes the ophthalmic treatment apparatus 10, an image unit 120, an image analysis unit 130, a beam generation unit 150, a beam delivery unit 160, an input unit 180, and a control unit 190. The ophthalmic treatment apparatus 10 according to the present invention is used to treat, in particular, the retina R, that is, the curvature (C) region of an eyeball O.

A contact lens 110 comes in contact with the eyeball O and enables the visibility of the retina R to be secured. That is, the contact lens 110 enables an operator to view the retina R. The contact lens 110 is disposed between the eyeball O and the collimation unit 168 of the beam delivery unit 160 to be described later.

The image unit 120 is provided to perform a computed tomography scan on the eyeball O. In an embodiment, Optical Coherence Tomography (OCT), etc. may be used as the image unit 120. The image unit 120 may perform a computed tomography scan on the eyeball O using some elements of the beam delivery unit 160. In this case, the image unit 120 performs a computed tomography scan on the eyeball O along an optical axial line (OA: refer to FIGS. 3 and 4) to which a beam for treatment is radiated. That is, the image unit 120 performs a computed tomography scan on the retina (R) region of the eyeball O in a direction perpendicular to the plane F of the focal spot of a beam for treatment (refer to FIGS. 3 and 4).

The image analysis unit 130 analyzes an image of the eyeball O captured by the image unit 120. The image analysis unit 130 may obtain three-dimensional information, including curvature C of the retina (R) region, by analyzing a tomographic image of the retina (R) region of the eyeball O received from the image unit 120 so that the location of the plane F of a focal spot according to the curvature C of the retina R is measured. In general, shape and curvature characteristics of a retina region are a little different in each patient. In the present embodiment, characteristic information, such as a shape and curvature C of the retina of a patient, can be accurately analyzed and the location of the plane F of a focal spot can be determined using the image analysis unit.

The beam generation unit 150 generates a beam for treatment based on an input signal applied by the input unit 180. In an embodiment of the present invention, a laser medium or a laser diode for generating a laser may be used as the beam generation unit 150 so that a laser is used as a beam for treatment. In this case, the beam for treatment generated by the beam generation unit 150 may be various depending on the type of light source (not illustrated).

The beam for treatment generated by the beam generation unit 150 has a wavelength band capable of treating a lesion of the eyeball O. That is, the beam for treatment generated by the beam generation unit 150 may have a wavelength band of 532 nm to 1064 nm. However, the beam for treatment generated by the beam generation unit 150 may have a wavelength band of less than 532 nm or more than 1064 nm depending on a treatment purpose or a lesion, that is, the subject of treatment, in addition to the aforementioned wavelength band of 532 nm to 1064 nm.

Figure 3:
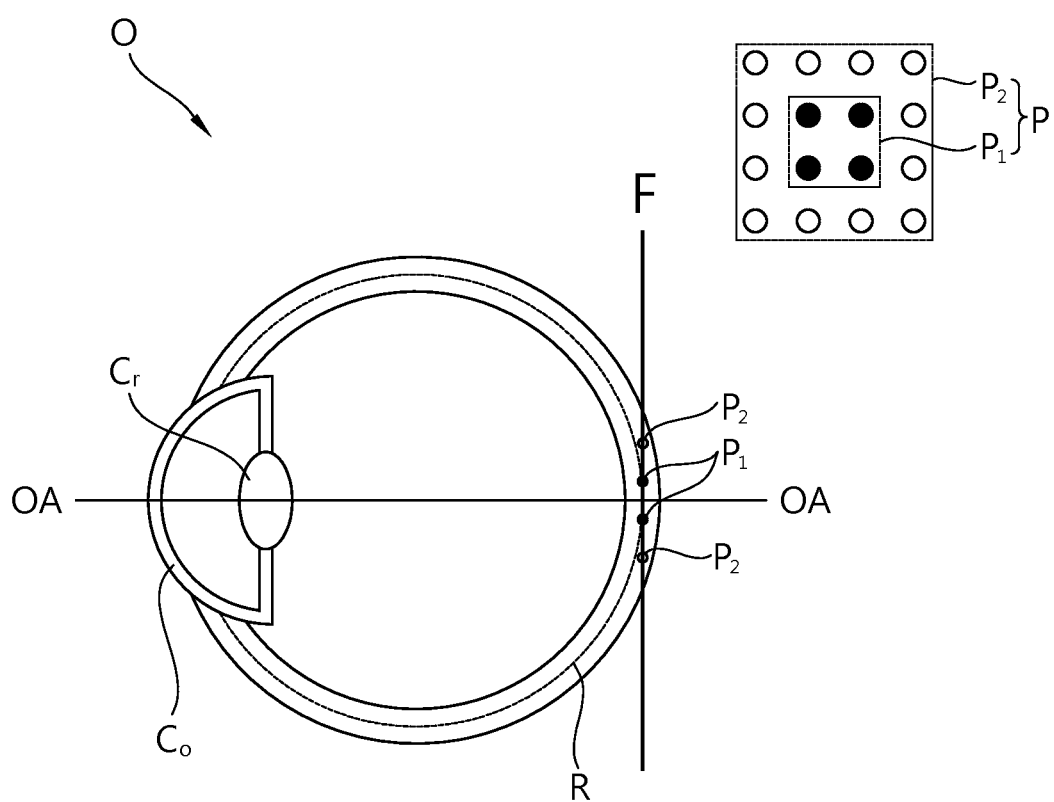
FIG. 3 is a schematic diagram of the plane F of a focal spot that are commonly formed in the retina of an eyeball.
Figure 4:
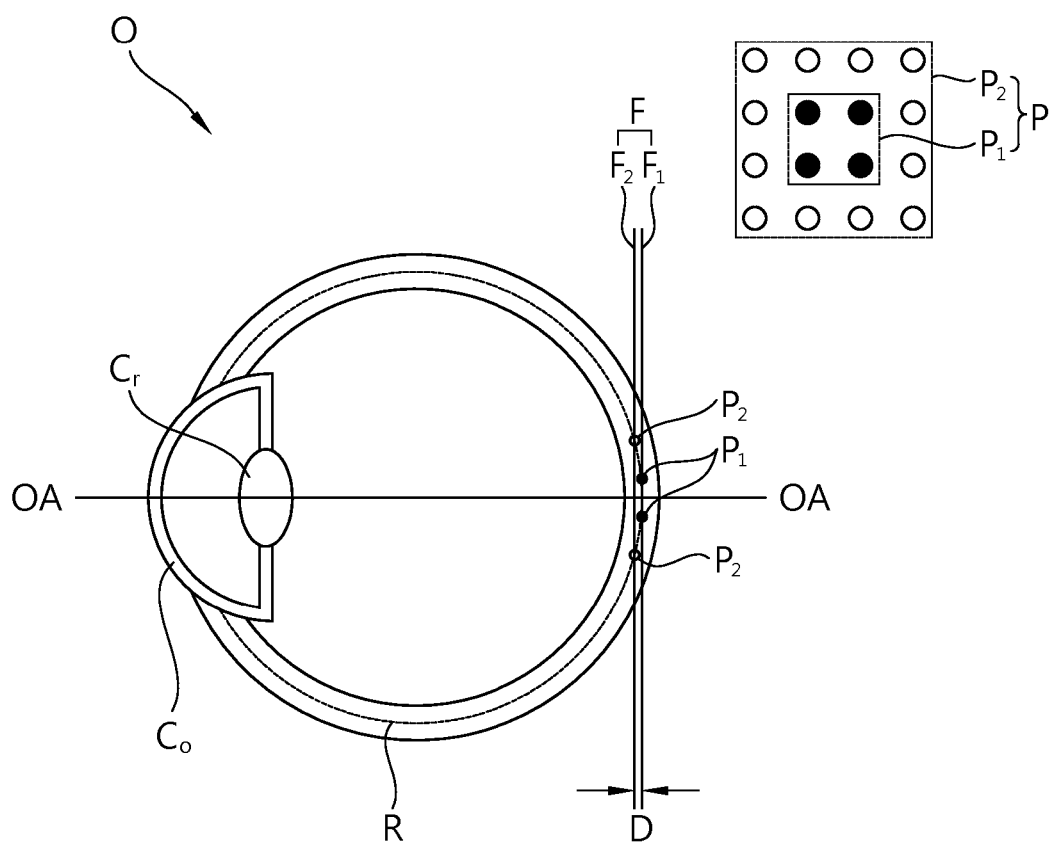
FIG. 4 is a schematic diagram of the plane F of a focal spot formed in the retina of an eyeball in accordance with an embodiment of the present invention.

FIG. 3 is a schematic diagram of the plane F of a focal spot that are commonly formed in the retina of an eyeball, and FIG. 4 is a schematic diagram of the plane F of a focal spot formed in the retina of an eyeball in accordance with an embodiment of the present invention.

As illustrated in FIGS. 3 and 4, the beam delivery unit 160 includes a first scanner 162, a second scanner 164, a beam splitter 166 and the collimation unit 168. The beam delivery unit 160 guides a beam for treatment, generated by the beam generation unit 150, to the retina (R) region of the eyeball O. The beam delivery unit 160 leads a beam for treatment so that the beam for treatment is radiated to the retina R through the cornea $C_o$ and eye lens $C_r$ of the eyeball O. For example, the beam delivery unit 160 using a conventional method and a method according to the present invention is described with reference to FIGS. 3 and 4.

The beam delivery unit 160 of FIG. 3 using the conventional method radiates a beam for treatment to the plane F of a focal spot irrespective of curvature C of a retina (R) region. That is, when the beam for treatment is radiated in the form of a pattern P including a reference pattern $P_1$ and a control pattern $P_2$, the beam delivery unit 160 radiates the reference pattern $P_1$ and the control pattern $P_2$ to the same plane F of the focal spot (In this case, the reference pattern may be a pattern placed at the central part of the entire radiation pattern to which the beam for treatment is radiated, and the control pattern may be a pattern placed at the edge of the reference pattern. Alternatively, the reference pattern may be a pattern placed at a retina location having a first depth, and the control pattern may be a pattern placed at a retina location having a second depth different from the first depth). If the beam delivery unit 160 radiates the control pattern $P_2$ to the same plane F of the focal spot as the reference pattern $P_1$ irrespective of the curvature C of the retina (R) region as described above, the focal spot of part of the beam for treatment is not placed in a lesion region although part of the focal spot of the beam for treatment is placed in the lesion region.

Meanwhile, the beam delivery unit 160 of FIG. 4 using the method of the present invention controls the location to which the beam for treatment including the reference pattern $P_1$ and the control pattern $P_2$ is radiated based on the curvature C of the retina (R) region. That is, the beam delivery unit 160 divides the plane F of the focal spot into a plane $F_1$ of a first focal spot and, based on data from the image unit 120 and the image analysis unit 130 and radiates the beam for treatment. The beam delivery unit 160 radiates the reference pattern $P_1$ to the plane $F_1$ of the first focal spot and radiates the control pattern $P_2$ to the plane $F_2$ of the second focal spot based on the curvature C of the retina R. As described above, the curvature C of the retina (R) region of the eyeball O is analyzed, the plane F of the focal spot is divided into the plane $F_1$ of the first focal spot and the plane $F_2$ of the second focal spot to which the reference pattern $P_1$ and the control pattern $P_2$ are respectively radiated, thereby being capable of improving treatment efficiency.

In an embodiment of the present invention, the beam delivery unit 160 includes the first scanner 162, the second scanner 164, the beam splitter 166, and the collimation unit 168. The first scanner 162 guides the beam for treatment provided by the beam generation unit 150 to the plane F of the focal spot. That is, assuming that an XY plane, that is, a direction perpendicular to the optical axial line of the beam for treatment, is the plane F of the focal spot, the first scanner 162 controls the location where the beam for treatment is radiated on the plane F of the focal spot.

The second scanner 164 controls the location of the focal spot of the beam for treatment incident from the first scanner 162 along the optical axial line OA. That is, the second scanner 164 controls the location of the focal spot of the beam for treatment in a Z axis, that is, a direction perpendicular to the XY plane. The second scanner 164 controls the location of the focal spot of the beam for treatment so that the beam for treatment is radiated to the plane $F_1$ of the first focal spot and the plane $F_2$ of the second focal spot in the Z axis. In an embodiment of the present invention, the second scanner 164 includes a beam extension lens 164a and a mobile lens 164b.

The beam extension lens 164a extends the beam for treatment that is incident from the first scanner 162. Furthermore, the mobile lens 164b relatively moves compared to the beam extension lens 164a so that the beam for treatment passing through the beam extension lens 164a is radiated along the optical axial line OA between the plane $F_1$ of the first focal spot and the plane $F_2$ of the second focal spot. The mobile lens 164b relatively moves compared to the beam extension lens 164a, so the beam for treatment is radiated to the plane $F_1$ of the first focal spot and the plane $F_2$ of the second focal spot along the optical axial line OA, that is, the Z axis. More specifically, the mobile lens 164b radiates the reference pattern $P_1$ and the control pattern $P_2$ of the pattern form P to the plane $F_1$ of the first focal spot and the plane $F_2$ of the second focal spot that are formed along the curvature C of the retina R.

The beam splitter 166 guides a beam for treatment, provided by the first scanner 162 and the second scanner 164, to the contact lens 110. Precisely, the beam splitter 166 guides the beam for treatment to the collimation unit 168. The collimation unit 168 guides the beam for treatment, provided by the beam splitter 166, to the contact lens 110. An object lens is used as the collimation unit 168.

The input unit 180 applies an input signal so that a beam for treatment is generated by the beam generation unit 150. Furthermore, the input unit 180 applies an input signal so that an image of the retina (R) region of the eyeball O is captured and formed by the image unit 120.

Finally, the control unit 190 controls the operation of the beam generation unit 150 so that a beam for treatment is generated based on an input signal applied by the input unit 180. Furthermore, the control unit 190 controls the operation of the image unit 120 so that a computed tomography scan is performed on the eyeball O based on an input signal applied by the input unit 180.

The control unit 190 of the present invention controls the operation of the beam delivery unit 160 so that the location of the plane F of the focal spot to which the beam for treatment is radiated is controlled based on the curvature C with respect to the retina (R) region of the eyeball O that has been photographed by the image unit 120. That is, the control unit 190 controls the operation of the beam delivery unit 160 such that the reference pattern $P_1$ and control pattern $P_2$ of the pattern form P are respectively radiated to the plane $F_1$ of the first focal spot and the plane $F_2$ of the second focal spot. In this case, the control unit 190 controls the operation of the beam delivery unit 160 so that the reference pattern $P_1$ and the control pattern $P_2$ are radiated based on a separation distance D between the plane $F_1$ of the first focal spot and the plane $F_2$ of the second focal spot that correspond to the curvature C of the retina R.

Figure 5:
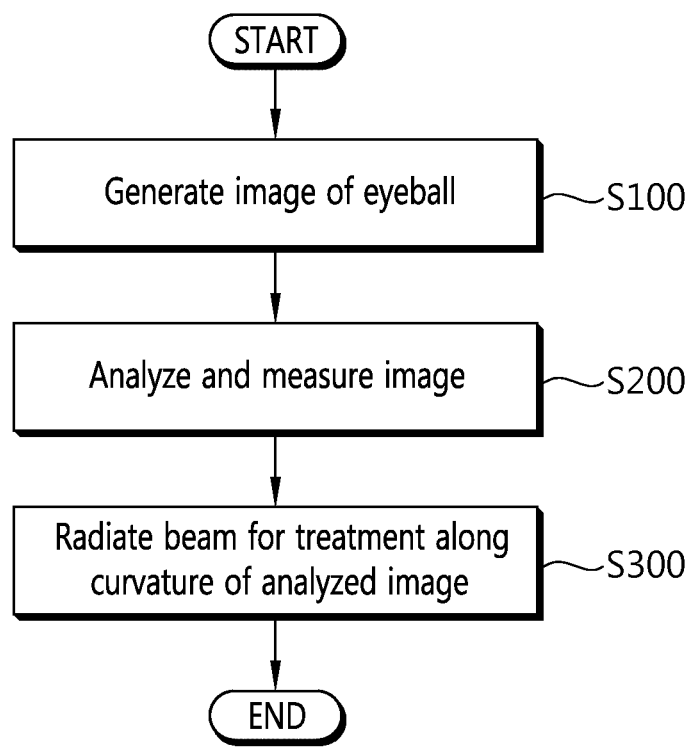
FIG. 5 is a control flowchart illustrating a method for radiating, by the ophthalmic treatment apparatus, a beam for treatment in accordance with an embodiment of the present invention.

FIG. 5 is a control flowchart illustrating a method for radiating, by the ophthalmic treatment apparatus, a beam for treatment in accordance with an embodiment of the present invention.

The method for radiating, by the ophthalmic treatment apparatus 10 configured as described above, a beam for treatment according to the present invention is described with reference to FIG. 5.

First, a computed tomography scan is performed on the eyeball O along the optical axial line OA of a beam for treatment using the image unit 120 (S100). An image of the eyeball O captured by the image unit 120 is transmitted to the image analysis unit 130. The image analysis unit 130 analyzes the image of the eyeball O and measures the curvature C of the retina (R) region (S200). In this case, the image analysis unit 130 analyzes the curvature C of the retina (R) region and measures the separation distance D between the plane $F_1$ of the first focal spot and the plane $F_2$ of the second focal spot to which the beam for treatment including the reference pattern $P_1$ and control pattern $P_2$ of the pattern form P is radiated.

The operation of the beam delivery unit 160 is controlled so that the beam for treatment is radiated based on the separation distance D between the plane $F_1$ of the first focal spot and the plane $F_2$ of the second focal spot that has been analyzed by the image analysis unit 130, that is, the curvature C of the analyzed image (S300).

As described above, curvature according to an image of an eyeball can be measured and analyzed, and the plane of a focal spot to which a beam for treatment is radiated can be controlled based on the curvature of the eyeball. Accordingly, the beam for treatment can be radiated to a location corresponding to the curvature of the eyeball, and thus treatment efficiency of the eyeball can be improved.

As described above, although the embodiments of the present invention have been described with reference to the accompanying drawings, those skilled in the art to which the present invention pertains will understand that the present invention may be implemented in other detailed forms without changing the technical spirit or indispensable characteristics of the present invention. Accordingly, it will be understood that the aforementioned embodiments are illustrative and not limitative from all aspects. The scope of the present invention is defined by the appended claims rather than the detailed description, and the present invention should be construed as covering all modifications or variations derived from the meaning and scope of the appended claims and their equivalents.

What is claimed is:

1. An ophthalmic treatment apparatus, comprising:
a beam generation unit which generates a beam for treatment; and
a beam delivery unit which guides the beam for treatment generated by the beam generation unit to a retina region of an eyeball; and
an imaging unit which generates an image of the retina region of the eyeball in a direction perpendicular to at least one plane of at least one focal spot of the beam for treatment that is guided by the beam delivery unit,
wherein the ophthalmic treatment apparatus controls the beam delivery unit so that a location of the at least one plane of the at least one focal spot to which the beam for treatment is radiated is controlled based on curvature of the retina region of the eyeball photographed by the image unit,
wherein the at least one plane includes a plane of a first focal spot and a plane of a second focal spot which is separated by a distance from the plane of the first focal spot, and the beam delivery unit radiates the beam for treatment to the retina region of the eyeball in a pattern comprising a plurality of focal spots, and
wherein a controller divides the pattern into a reference pattern located on the plane of the first focal spot and a control pattern located on the plane of the second focal spot and controls the beam delivery unit to radiate the first pattern onto the first focal spot and, after terminating radiation of the first pattern, to radiate the second pattern onto the second focal spot,
wherein the plane of the first focal spot forms a tangential plane in an arc of the retina region of the eyeball through which an optical axial line of the beam for treatment penetrates,
wherein the plane of the second focal spot is parallel to the plane of the first focal spot along the optical axial line and connects both ends of an arc formed with a contact point of the retina region interposed between the two sides,
wherein the separation distance between the plane of the first focal spot and the plane of the second focal spot corresponds to the curvature of the retina region of the eyeball,
wherein the ophthalmic treatment apparatus analyzes the image of the retina region of the eyeball transmitted by the image unit and measures the separation distance between the plane of the first focal spot and the plane of the second focal spot, and
wherein the ophthalmic treatment apparatus controls an operation of the beam delivery unit so that the beam for treatment is radiated to the plane of the first focal spot and the plane of the second focal spot based on the separation distance between the plane of the first focal spot and the plane of the second focal spot.

2. The ophthalmic treatment apparatus of claim 1, wherein the beam delivery unit comprises:
a first scanner which guides the beam for treatment generated by the beam generation unit to the at least one plane of the at least one focal spot;
a collimation unit which collimates the beam for treatment incident from the first scanner to the retina region of the eyeball; and
a second scanner which is disposed between the first scanner and the collimation unit and controls a location of the focal spot of the beam for treatment incident from the first scanner along the optical axial line of the beam for treatment.

3. The ophthalmic treatment apparatus of claim 2, wherein the second scanner comprises:
a beam extension lens which extends the beam for treatment incident from the first scanner; and
a mobile lens which relatively moves compared to the beam extension lens so that the beam for treatment passing through the beam extension lens is radiated along the optical axial line between the plane of the first focal spot and the plane of the second focal spot.

4. The ophthalmic treatment apparatus of claim 3, wherein the ophthalmic treatment apparatus analyzes the image of the retina region of the eyeball and measures the separation distance between the plane of the first focal spot and the plane of the second focal spot.

5. The ophthalmic treatment apparatus of claim 4, wherein the ophthalmic treatment apparatus relatively moves the mobile lens compared to the beam extension lens so that the pattern form of the beam for treatment is radiated to the plane of the first focal spot and the plane of the second focal spot based on the separation distance between the plane of the first focal spot and the plane of the second focal spot.

6. A method for radiating, by an ophthalmic treatment apparatus, a beam for treatment, the method comprising steps of:
(a) generating an image of a retina region of an eyeball in a direction perpendicular to at least one plane of at least one focal spot to which a beam for treatment is radiated, the at least one plane including a plane of a first focal spot and a plane of a second focal spot which is separated by a distance from the plane of the first focal spot;
(b) analyzing curvature of the image and measuring a location where the beam for treatment is radiated and measuring the separation distance between the plane of the first focal spot and the plane of the second focal spot, wherein the separation distance between the plane of the first focal spot and the plane of the second focal spot corresponds to the curvature of the retina region of the eyeball; and (c) radiating the beam for treatment along the curvature in accordance with the curvature of the image, wherein in step (c), a beam delivery unit guiding the beam for treatment radiates the beam for treatment to the retina region of the eyeball in a pattern comprising a plurality of focal spots, and wherein the pattern is divided into a reference pattern located on the plane of the first focal spot and a control pattern located on the plane of the second focal spot, and the beam delivery unit radiates the first pattern onto the first focal spot and, after terminating radiation of the first pattern, radiates the second pattern onto the second focal spot, wherein the plane of the first focal spot forms a tangential plane in an arc of the retina region of the eyeball through which an optical axial line of the beam for treatment penetrates, wherein the plane of the second focal spot is parallel to the plane of the first focal spot along the optical axial line and connects both ends of an arc formed with a contact point of the retina region interposed between the two sides, and wherein the ophthalmic treatment apparatus analyzes the image of the retina region of the eyeball and radiates the beam for treatment to the plane of the first focal spot and the plane of the second focal spot based on the separation distance between the plane of the first focal spot and the plane of the second focal spot.

* * * * *